United States Patent [19]

Holtkamp

[11] Plant 4,546

[45] Jun. 17, 1980

[54] AFRICAN VIOLET PLANT

[75] Inventor: Reinhold Holtkamp, Isselburg, Fed. Rep. of Germany

[73] Assignee: Gessellschaftsvertrag uber die Erfindergemeinschaft "Optimara", Isselburg, Fed. Rep. of Germany

[21] Appl. No.: 15,821

[22] Filed: Feb. 27, 1979

[51] Int. Cl.[2] ..... A01H 5/00

[52] U.S. Cl. ..... Plt./69

[58] Field of Search ..... Plt./69

*Primary Examiner*—Robert E. Bagwill
*Assistant Examiner*—James R. Feyrer
*Attorney, Agent, or Firm*—Donald D. Jeffery

[57] ABSTRACT

An African violet known by the cultivar name Hawaii and characterized by the combined characteristics of large, star-shaped, blue flowers which have white, wavy edges, with additional small petals occasionally occurring at the flower center; strong upright flower stems, and by its medium size leaves which have serrated edges.

1 Drawing Figure

The present invention comprises a new and distinct cultivar of African violet plant, botanically known as *Saintpaulia ionantha,* and hereinafter referred to by the cultivar name Hawaii. Hawaii has very large star-shaped blue flowers with white edges which are slightly waved. The strong and upright flower stems carry up to seven and more single flowers. Frequently, the flowers have additional petals connected at the center to the stem part carrying the filaments. The flowers are non-dropping. These traits in combination were not present in previously available commercial cultivars.

The new cultivar was originated from a cross made in a controlled breeding program in Isselburg, Rhineland, Germany. The female, or seed parent was a cultivar designated E 861Z blue, an unpatented cultivar. The male, or pollen parent was designated BES I blue star, also unpatented.

The new cultivar Hawaii was discovered and selected as a flowering plant within the progeny of the stated cross by me in a controlled environment in Isselburg, Rhineland, Germany.

Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of Hawaii, which in combination distinguish this African violet as a new and distinct cultivar:

(1) Strong upright flower stems.

(2) 5–7 large star-shaped blue flowers with white wave edges, with the flowers being non-dropping.

(3) A few flowers frequently have additional petals joined with the stem part carrying the filaments.

(4) Medium size leaves having serrated edges and fairly hairy.

The accompanying photographic drawing shows a typical specimen plant of the new cultivar. The colors appearing in the photograph are as true as possible with color illustrations of this type.

In the following description, color references are made both to the Royal Horticultural Society color chart (RHS), and to the Horticultural Color Chart issued by Wilson Colour Ltd. (HCC). The use of both of these references is for the purpose of providing the most accurate values possible.

Botanical classification: *Saintpaulia ionantha,* Ramat, cv, Hawaii.

Parentage:

*Male parent.*—E 86/Z blue.

*Female parent.*—BES I blue star.

Propagation: The new cultivar holds its distinguishing characteristics through successive propagations by leaf cuttings and by division of shoots.

Plant: From 9 cm. to 12 cm. tall when grown in pots, and approximately 25–30 cm. in diameter when fully grown.

Leaves:

*General form.*—Round to oval.

*Diameter.*—55–65 mm.

*Texture.*—Very tender, hairy, velvety.

*Aspect.*—Edges are medium to strongly serrated.

*Veins.*—Well pronounced under and upperside, with the veins on the underside being green-brownish to red-brown.

*Color (upperside).*—HCC 00962 (Parsley Green); center of leaves medium green.

*Color (underside).*—HCC 00761/2 (Lavender Green).

*Petiole.*—Greenish-brown to dark brown, hairy.

Flowers:

*Buds.*—Bell-shaped, 8–10 mm. before opening, color, violet RHS 87 between B and C.

*Sepals.*—5 in number, 6–7 mm. long, spear-shaped. Color: medium green-brownish. Calyx: flat funnel-shaped. Aspect: flower stem and receptacle are connected. Peduncle: hairy, erect, brownish.

Individual flowers:

*Size.*—45–55 mm. when mature; slightly funnel-shaped.

*Color.*—Upperside: HCC 738 (Victoria Violet). Underside: RHS 87A.

*Borne.*—Up to 7 flowers per stem.

*Shape.*—Normally five petals of equal size, star-shaped; some flowers have additional petals in the center; some flowers have six petals; edges of petals are wavy.

*Arrangement.*—Flower stems initially come up in the center; with fully open flowers; the early stems tend to bend sideward to accommodate further stems in center.

*Flowering time.*—8 weeks after potting a well developed starter, the first flowers appear; full blooming occurs in 10–11 weeks.

Reproductive organs:

*Stamens.*—4–5 in number; the stamens have short stems, greenish-light yellow in color, and on a few stems are small petal-like parts, similar in color to the flowers.

*Anthers.*—8–10 anthers, color RHS 9A.

*Styles.*—Color HCC 738 (Victoria Violet).

*Pollen color.*—RHS 8D.

Roots: Normally developed; white when young, turning brownish when older.

Disease resistance: No disease noticed to date.

General observations: Hawaii has large star-shaped blue flowers with white edges. A few flowers tend to semi-double but most are single with five petals of equal size. The flowers with more petals tend to have six large petals and additional small petals which are connected to the stems carrying the filaments. The flower buds are bell-shaped and the white edges of the flower are already visible on the small petals. The mature flowers do not drop.

I claim:

1. A new and distinct cultivar of African violet, as shown and described, known by the cultivar name Hawaii and characterized by the combined characteristics of large, star-shaped, blue flowers which have white, wavy edges, with additional small petals occasionally occurring at the flower center; strong upright flower stems, and by its medium size leaves which have serrated edges.

* * * * *

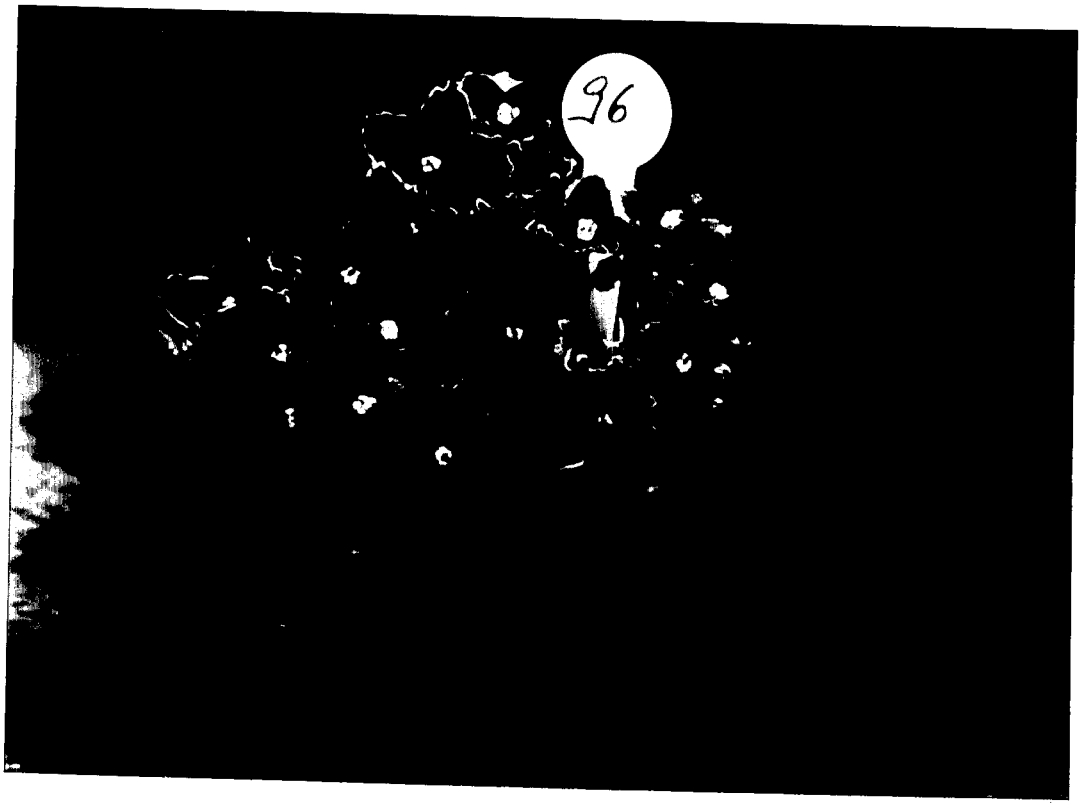
96